(12) United States Patent
Wang

(10) Patent No.: US 6,776,160 B2
(45) Date of Patent: Aug. 17, 2004

(54) ALL-IN-ONE INTAKE VALVE

(75) Inventor: Chih Hua Wang, I Lan Hsien (TW)

(73) Assignee: Galemed Corporation, I Lan Hsien (TW)

( * ) Notice: Subject to any disclaimer, the term of this patent is extended or adjusted under 35 U.S.C. 154(b) by 114 days.

(21) Appl. No.: 10/144,220

(22) Filed: May 14, 2002

(65) Prior Publication Data

US 2003/0213486 A1 Nov. 20, 2003

(51) Int. Cl.[7] .......................... A62B 7/00; A61M 16/00
(52) U.S. Cl. ............................ 128/205.13; 128/202.28; 128/202.29; 128/203.11
(58) Field of Search ................ 128/202.28, 202.29, 128/203.11, 203.28, 203.29, 205.13, 205.14, 205.15, 205.17, 205.24

(56) References Cited

U.S. PATENT DOCUMENTS

| 5,427,091 A | * | 6/1995 | Phillips ................ 128/205.15 |
| 5,558,371 A | * | 9/1996 | Lordo ..................... 285/114 |
| 5,791,340 A | * | 8/1998 | Schleufe et al. ....... 128/203.28 |
| 5,803,074 A | * | 9/1998 | Pope .................... 128/205.24 |
| 6,427,687 B1 | * | 8/2002 | Kirk ..................... 128/203.11 |
| 6,578,574 B1 | * | 6/2003 | Køhnke ................. 128/203.11 |

* cited by examiner

*Primary Examiner*—Henry Bennett
*Assistant Examiner*—Mital Patel
(74) *Attorney, Agent, or Firm*—Charles E. Baxley

(57) ABSTRACT

An intake valve includes a bladder having a face piece coupled to one end and an opening formed in the other end, a cover attached to the other end of the bladder and having a port coupled to an air reservoir and having a hub coupled to a container, which may be used for pumping air into the bladder when the air in the air reservoir has been consumed. The cover has a check valve for air to flow into the cover when the container is expanded, and for pumping air into the bladder when the container is squeezed. Another check valve may be used for outward flowing of excess air.

4 Claims, 5 Drawing Sheets

ALL-IN-ONE INTAKE VALVE

BACKGROUND OF THE INVENTION

1. Field of the Invention

The present invention relates to an intake valve, and more particularly to an all-in-one intake valve assembly.

2. Description of the Prior Art

Typical intake valves comprise a expandable bladder including one end for coupling to a mouth piece or a face piece that may be used for engaging onto the nose and/or the mouth of the patients, and the other end for coupling to the oxygen suppliers and for supplying the oxygen to the patients. However, the pressure within the bladder may not be balanced. In addition, when the oxygen has been consumed, the intake valves may no longer be used for pumping air or oxygen into the patients.

The present invention has arisen to mitigate and/or obviate the afore-described disadvantages of the conventional intake valves.

SUMMARY OF THE INVENTION

The primary objective of the present invention is to provide an intake valve assembly including a device for balancing the pressure within the bladder.

The other objective of the present invention is to provide an intake valve assembly including a structure for pumping air or oxygen into the patients when the oxygen or the air reservoir has been consumed.

In accordance with one aspect of the invention, there is provided an intake valve assembly comprising a bladder including a first end, and including a second end having an opening formed therein, a face piece coupled to the first end of the bladder, a cover attaching to the second end of the bladder, the cover including a port for coupling to an air reservoir and for receiving air therefrom, and the cover including a hub provided therein, and a container coupled to the hub for receiving excess air from the air reservoir when the bladder is filled with air, and for pumping air into the bladder when required.

The cover includes a first check valve provided therein and arranged for allowing air to flow into the cover when the container is expanded, and for allowing air to flow into the bladder when the container is squeezed by the users.

The cover includes a second check valve provided therein and arranged for allowing the air to flow out of the cover when the container and the bladder have been filled with the air and when excess air has been supplied to the cover and the bladder.

A cap is further provided and attached to the second end of the bladder, the cover is secured onto the cap and including a space formed and defined between the cover and the cap.

The cap includes a check valve provided therein and arranged for allowing air to flow into the bladder and for preventing the air from flowing out of the bladder via the check valve. The check valve includes at least one passage formed in the cap, and a valve flap secured to the cap for selectively blocking the passage of the cap.

The cap includes a hub provided therein, the valve flap includes a stud extended therefrom and engaged into the hub of the cap for securing the valve flap to the cap.

The bladder includes a peripheral flange provided on the second end thereof for forming and defining the opening thereof, the peripheral flange includes a peripheral recess formed therein, the cap includes a peripheral rib extended radially outward therefrom for engaging into the peripheral recess of the peripheral flange and for securing the cap to the bladder.

Further objectives and advantages of the present invention will become apparent from a careful reading of a detailed description provided hereinbelow, with appropriate reference to accompanying drawings.

DETAILED DESCRIPTION OF THE PREFERRED EMBODIMENTS

Figure 1:
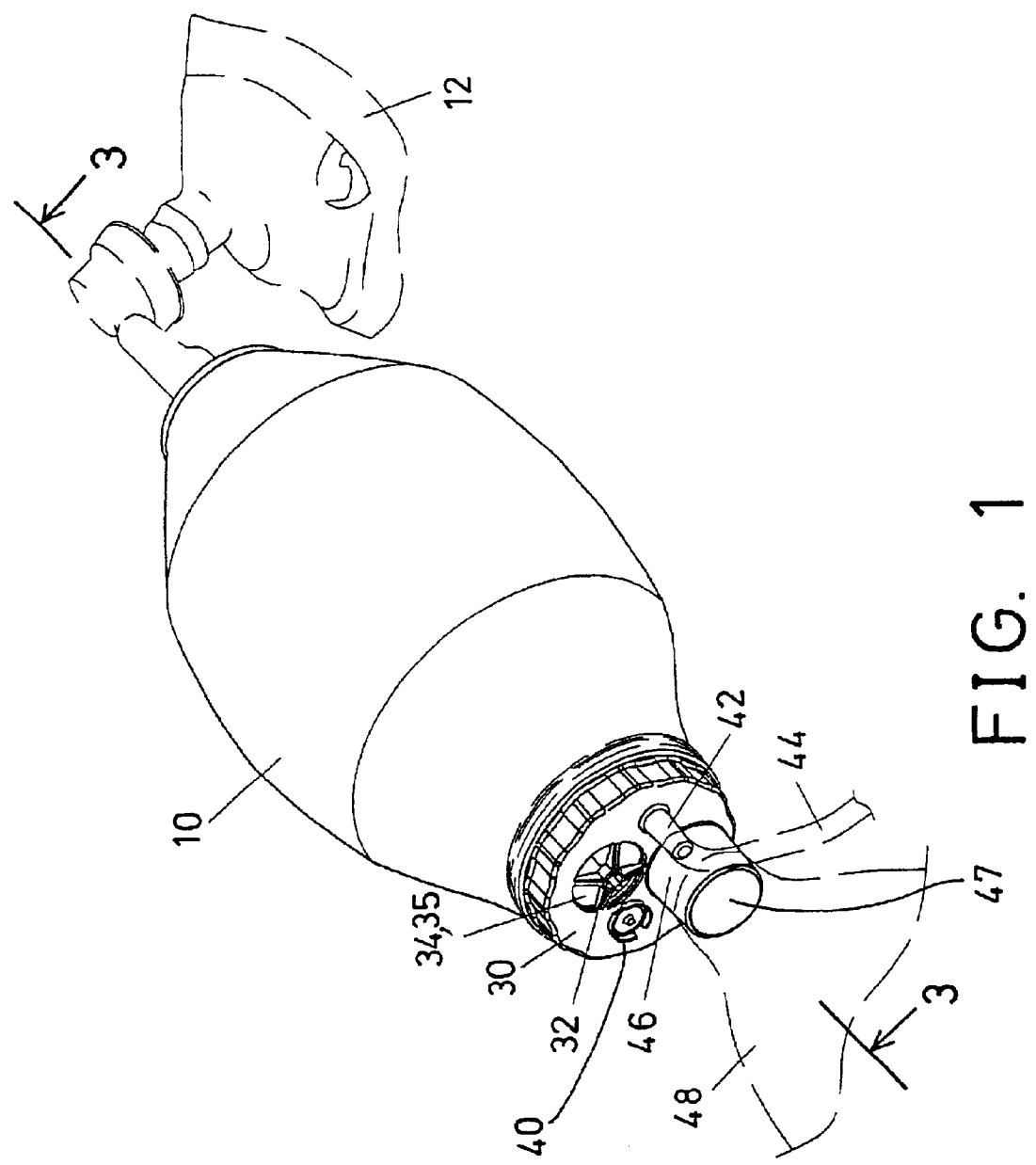
FIG. 1 is a partial perspective view of an intake valve assembly in accordance with the present invention.
Figure 2:
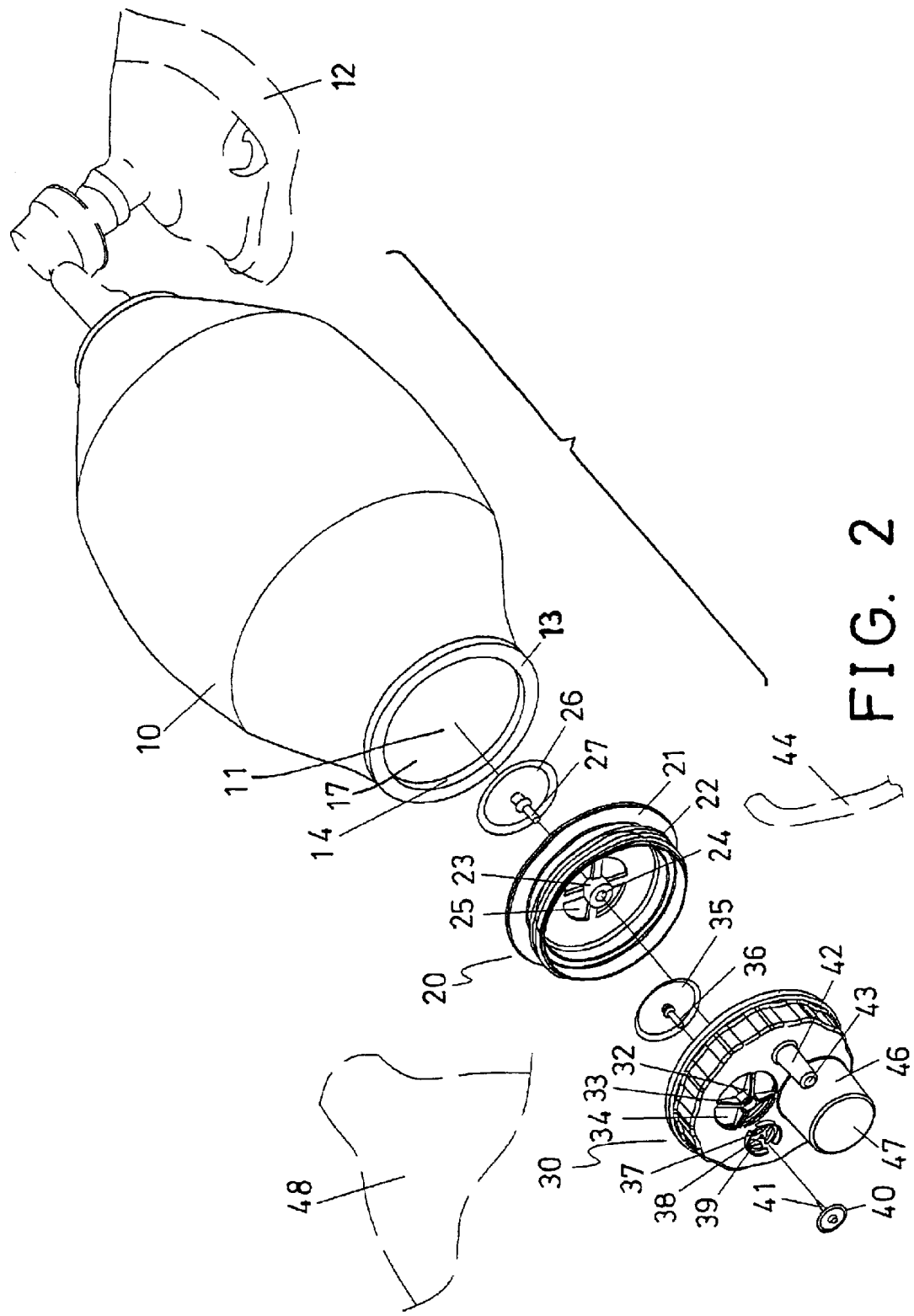
FIG. 2 is a partial exploded view of the intake valve assembly.
Figure 3:
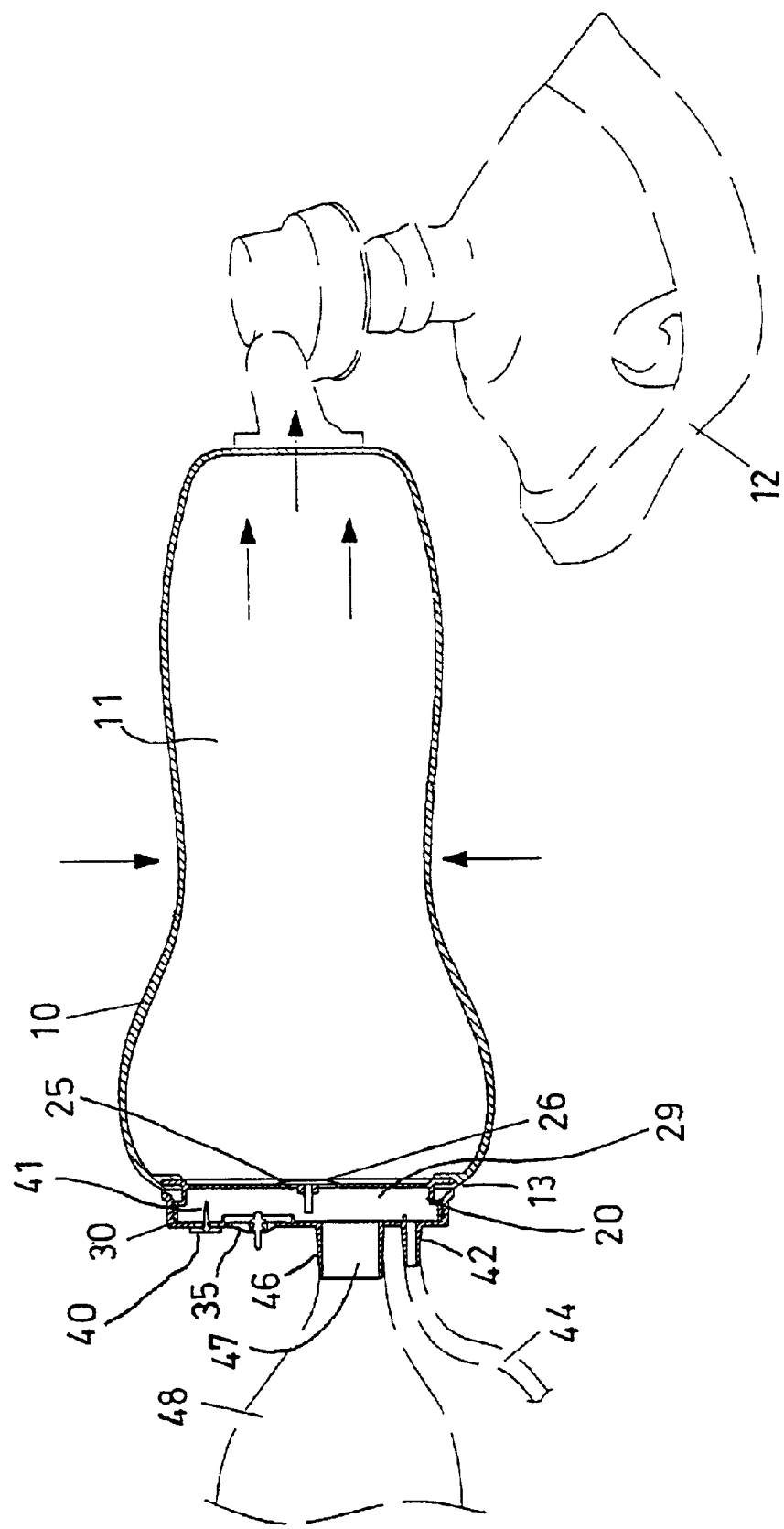
FIG. 3 is a partial cross sectional view taken along lines 3—3 of FIG. 1.

Referring to the drawings, and initially to FIGS. 1–3, an intake valve, such as an all-in-one intake valve assembly in accordance with the present invention comprises a bladder 10 including a chamber 11 formed therein for receiving air or oxygen and including one end coupled to a mouth piece or a face piece 12 which may be used for engaging onto the nose and/or the mouth of the patients (FIG. 5), and for pumping the air or the oxygen into the nose and/or the mouth of the patients. The other end of the bladder 10 includes an opening 17 formed therein and formed or defined by a peripheral flange 13.

Figure 4:
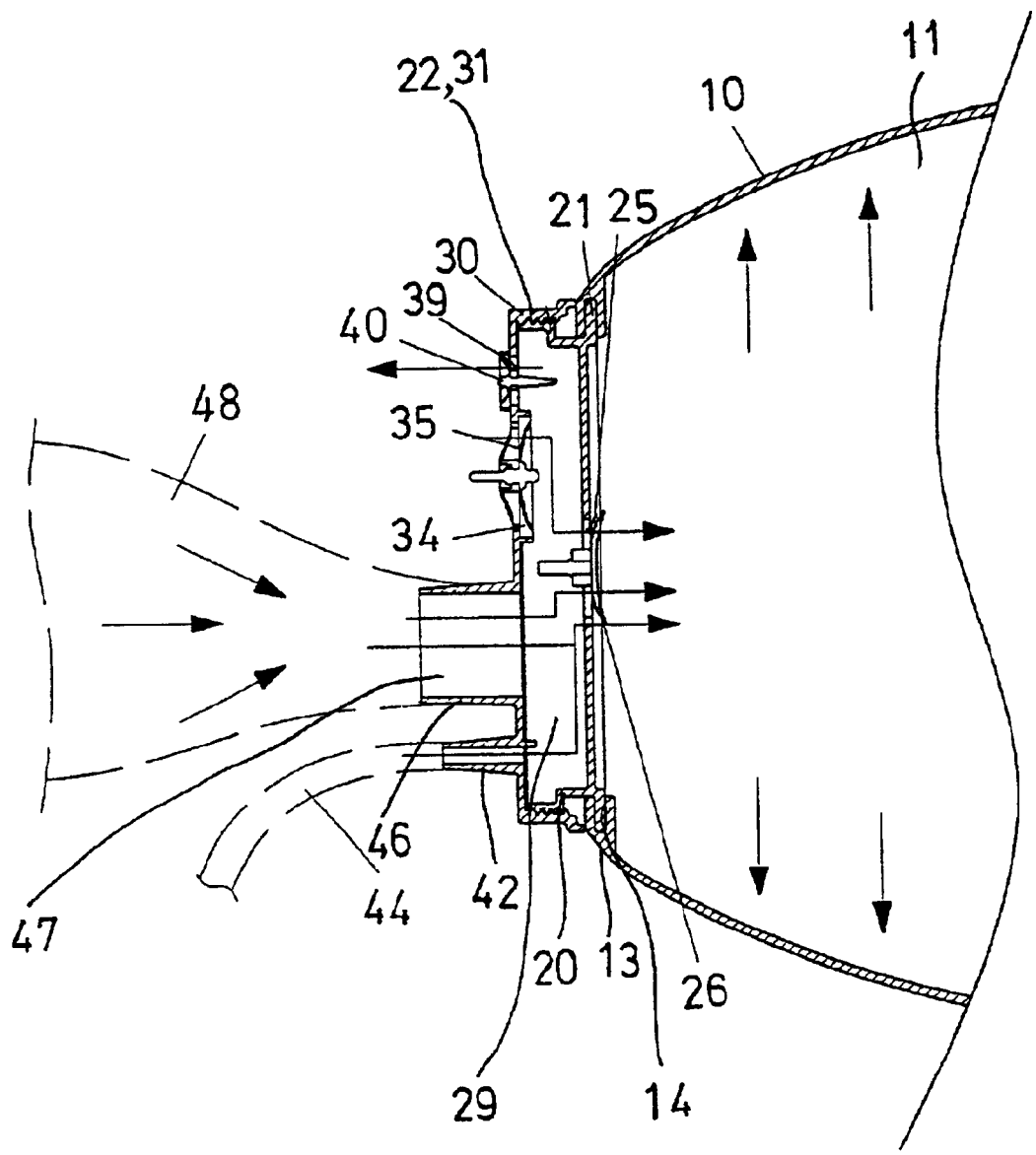
FIG. 4 is an enlarged partial cross sectional view illustrating the operation of the intake valve assembly.

As best shown in FIGS. 2–4, the peripheral flange 13 of the bladder 10 includes a peripheral recess 14 formed therein. A cap 20 includes a peripheral rib 21 extended radially outward therefrom for engaging into the peripheral recess 14 of the peripheral flange 13, and for securing the cap 20 to the bladder 10. The cap 20 includes an outer thread 22 formed thereon, and a hub 23 and one or more passages 25 provided therein, such as provided in the center portion thereof. The cap 20 may be used for blocking the opening 17 of the bladder 10, and the passages 25 of the cap 20 are provided for allowing air or oxygen or the like to flow into the bladder 10.

The hub 23 includes a bore 24 formed therein for receiving a center stud 27 of a valve flap 26. The valve flap 26 may be used for selectively blocking the passages 25 of the cap 20, and for forming a check valve to control the inward flowing of the air or the oxygen or the other fluid into the bladder 10. For example, as shown in FIG. 3, when the bladder 10 is squeezed, the fluid in the chamber 11 of the bladder 10 may force the valve flap 26 to enclose the passages 25 of the cap 20, and to prevent the fluid from flowing out through the passages 25 of the cap 20, and to force the air or oxygen to flow out to the face piece 12.

It is preferable that the bladder 10 is made of rubber or the other resilient materials, for allowing the bladder 10 to be expanded or recovered when the bladder 10 is released, or when the users no longer squeeze the bladder 10. Accordingly, when the bladder 10 is released, the pressure in the bladder 10 will be decreased, and the air or fluid may thus be forced or drawn into the bladder 10 via the passages 25 of the cap 20, against the spring force or the resilience of the valve flap 26. The air or fluid flowing into the bladder 10 may then be pumped to the face piece 12 again when the bladder 10 is squeezed by the users.

A cover 30 includes an inner thread 31 (FIG. 4) provided therein for threading with the outer thread 22 of the cap 20, and for detachably securing the cover 30 to the cap 20, and thus to the bladder 10, and for forming or defining a space 29 between the cover 30 and the cap 20. The cover 30 also includes a hub 32 and one or more apertures 34 provided therein, such as provided in the center portion or in the peripheral portion thereof. The apertures 34 of the cover 30 are provided for allowing air or oxygen or the like to flow into the space 29 of the cover 30 and/or of the cap 20.

The hub 32 includes a bore 33 formed therein for receiving a center stud 36 of a valve flap 35. The valve flap 35 may be used for selectively blocking the apertures 34 of the cover 30, and for forming a check valve to control the inward flowing of the air or the oxygen or the other fluid into the space 29 of the cover 30. For example, as shown in FIG. 3, when the pressure in the space 29 of the cover 30 is greater than that of the outer portion of the cover 30, the fluid in the space 29 of the cover 30 may force the valve flap 35 to enclose the apertures 34 of the cover 30, and to prevent the fluid from flowing out through the apertures 34 of the cover 30, and to force the air or oxygen to flow into the bladder 10 through the valve flap 26.

On the contrary, when the pressure in the space 29 of the cover 30 is decreased, for example, when the bladder 10 is expanded or recovered and when the air or fluid flows through the passages 25 of the cap 20 and flow into the bladder 10, the air or fluid may flow into the space 29 of the cover 30 via the apertures 34 of the cover 30, against the spring force or the resilience of the valve flap 35, such that the air or the other fluid outside the cover 30 may flow into the space 29 of the cover 30 via the apertures 34 of the cover 30.

The cover 30 includes a hub 46 for coupling to a container 48, such as a resilient container 48 for receiving the air or the oxygen or the other fluid. The hub 46 includes a bore 47 formed therein for allowing the air or the oxygen or the other fluid to flow into and out of the container 48. It is also preferable that the container 48 is made of rubber or the other resilient materials, for allowing the container 48 to be expanded or recovered when the container 48 is released, or when the container 48 has not been squeezed by the users.

The cover 30 further includes a port 42 having a bore 43 formed therein for coupling to a air or oxygen or the other fluid reservoir 45 (FIG. 5) with a hose 44 or the like, for allowing the air or oxygen or the other fluid to flow from the reservoir 45 to the space 29 of the cover 30 and then to flow into the bladder 10. The check valve formed by the valve flap 35 may block the apertures 34 of the cover 30 for preventing the air or the oxygen from flowing out of the space 29 of the cover 30. The check valve formed by the valve flap 26 allows the air or the oxygen to flow into the bladder 10.

The cover 30 further includes another hub 37 and one or more orifices 39 provided therein, such as provided in the peripheral portion thereof, and spaced from the apertures 34 of the cover 30. The hub 37 includes a bore 38 formed therein for receiving a center stud 41 of a valve flap 40. The valve flap 40 may be used for selectively blocking the orifices 39 of the cover 30, and for forming a check valve to control the outward flowing of the air or the oxygen or the other fluid into the space 29 of the cover 30. For example, the fluid or the air or the oxygen in the space 29 of the cover 30 may flow out through the orifices 39 of the cover 30 when the air or fluid is over supplied to the bladder 10 and the space 29 of the cover 30.

Figure 5:
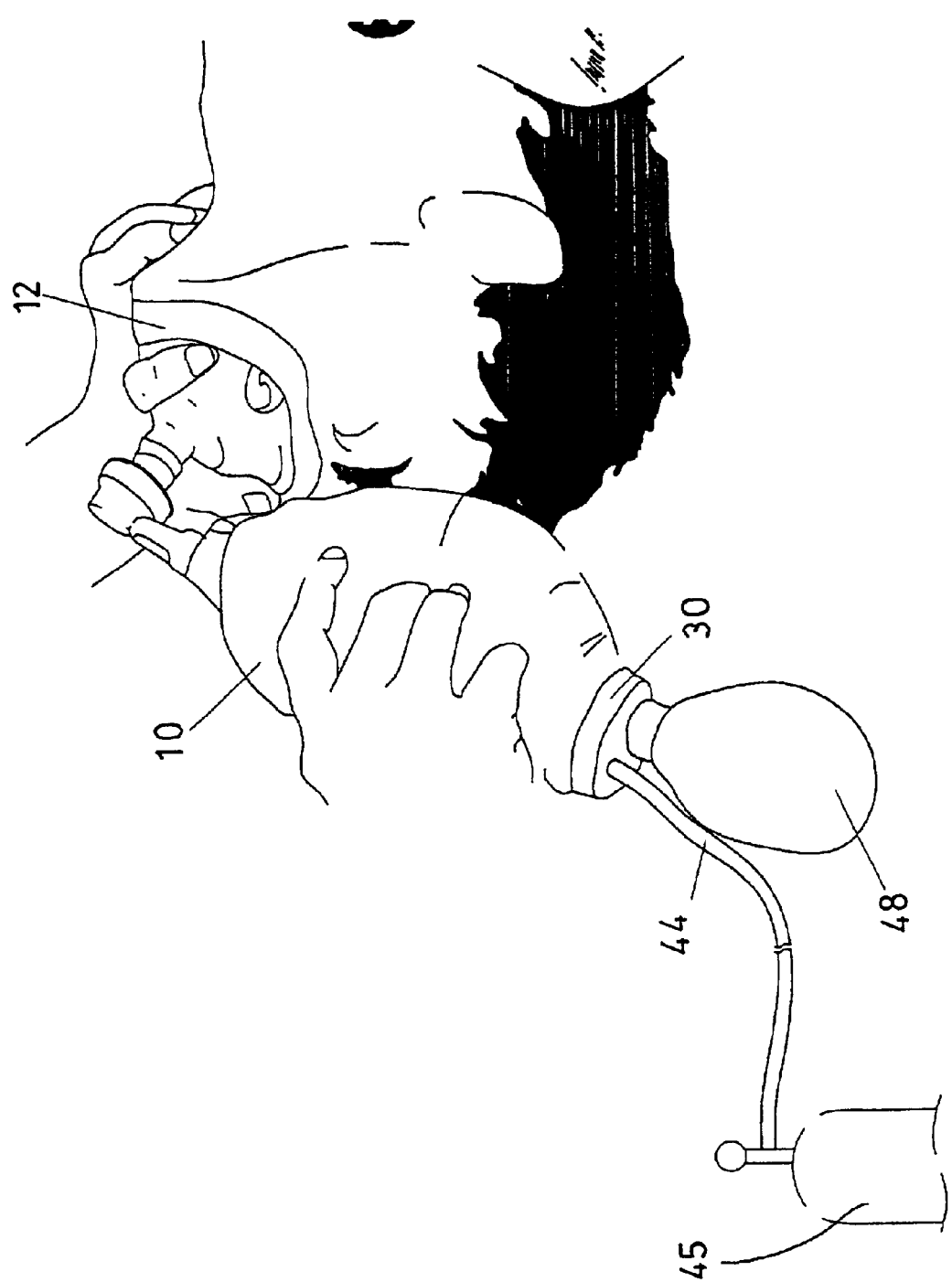
FIG. 5 is a partial perspective view illustrating the operation of the intake valve assembly.

In operation, as shown in FIG. 5, the face piece 12 may be engaged onto the nose and/or the mouth of the patient. The fluid from the reservoir 45 may flow into the space 29 of the cover 30 and then may flow into the bladder 10, for allowing the air or the fluid in the bladder 10 to be pumped into the patients. When the bladder 10 has been filled with the air or the fluid, the excess air or fluid may flow into the container 48 and stored in the container 48 for further use. When the container 48 has also been filled with the air or fluid, the excess air of fluid may flow out of the cover 30 against the valve flap 40 (FIG. 4). Accordingly, the pressure in the bladder 10 and/or in the container 48 and/or in the space 29 of the cover 30 may be balanced.

When the air or the fluid in the reservoir 45 has been consumed, the users may squeeze the container 48 to force the air from the container 48 to the bladder 10. In addition, when the container 48 is expanded or is recovered, the air outside the bladder 10 and the cover 30 may be drawn into the space 29 of the cover 30 via the apertures 34 of the cover 30, and may then be forced into the bladder 10 when the container 48 is squeezed by the users, such that the container 48 may be used to pump air into the bladder 10 in a reciprocating action when the air or the fluid in the reservoir 45 has been consumed.

Accordingly, the intake valve assembly in accordance with the present invention includes a device or a structure for balancing the pressure within the bladder, and for pumping air or oxygen into the patients when the oxygen or the air reservoir has been consumed.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. An intake valve assembly for attaching to a bladder, said intake valve assembly comprising:

a cap for attaching to the bladder, said cap including a first check valve provided therein and arranged for allowing air to flow into the bladder and for preventing the air from flowing out of the bladder via said first check valve when the bladder is squeezed, a cover attaching to and secured onto said cap and including a space formed and defined between said cover and said cap, said cover including a port for coupling to an air reservoir and for receiving air therefrom, and said cover including a hub provided therein, and including a second check valve provided therein and arranged for allowing air to flow into said cover, and said cover including a third check valve provided therein and arranged for allowing the air to flow out of said cover when the bladder has been filled with the air, and a container coupled to said hub for receiving excess air from the air reservoir.

2. The intake valve assembly according to claim 1, wherein said first check valve includes at least one passage formed in said cap, and a valve flap secured to said cap for selectively blocking said at least one passage of said cap.

3. The intake valve assembly according to claim 2, wherein said cap includes a hub provided therein, said valve flap includes a stud extended therefrom and engaged into said hub of said cap for securing said valve flap to said cap.

4. The intake valve assembly according to claim 1, wherein said cap includes a peripheral rib extended radially outward therefrom for engaging with the bladder.

* * * * *

(12) EX PARTE REEXAMINATION CERTIFICATE (7569th)
United States Patent
Wang

(10) Number: US 6,776,160 C1
(45) Certificate Issued: Jun. 22, 2010

(54) ALL-IN-ONE INTAKE VALVE

(75) Inventor: Chih Hua Wang, I Lan Hsien (TW)

(73) Assignee: Galemed Corporation, I Lan Hsien (TW)

Reexamination Request:
No. 90/010,597, Jul. 8, 2009

Reexamination Certificate for:
Patent No.: 6,776,160
Issued: Aug. 17, 2004
Appl. No.: 10/144,220
Filed: May 14, 2002

(51) Int. Cl.
*A61M 16/00* (2006.01)
*A62B 7/00* (2006.01)

(52) U.S. Cl. .................. 128/205.13; 128/202.28; 128/202.29; 128/203.11

(58) Field of Classification Search .............. None
See application file for complete search history.

(56) References Cited

U.S. PATENT DOCUMENTS

| 5,163,424 A | 11/1992 | Kohnke |
| 5,427,091 A | 6/1995 | Phillips |
| 5,791,340 A | 8/1998 | Schleufe et al. |
| 6,578,574 B1 | 6/2003 | Kohnke |

*Primary Examiner*—Aaron J. Lewis

(57) ABSTRACT

An intake valve includes a bladder having a face piece coupled to one end and an opening formed in the other end, a cover attached to the other end of the bladder and having a port coupled to an air reservoir and having a hub coupled to a container, which may be used for pumping air into the bladder when the air in the air reservoir has been consumed. The cover has a check valve for air to flow into the cover when the container is expanded, and for pumping air into the bladder when the container is squeezed. Another check valve may be used for outward flowing of excess air.

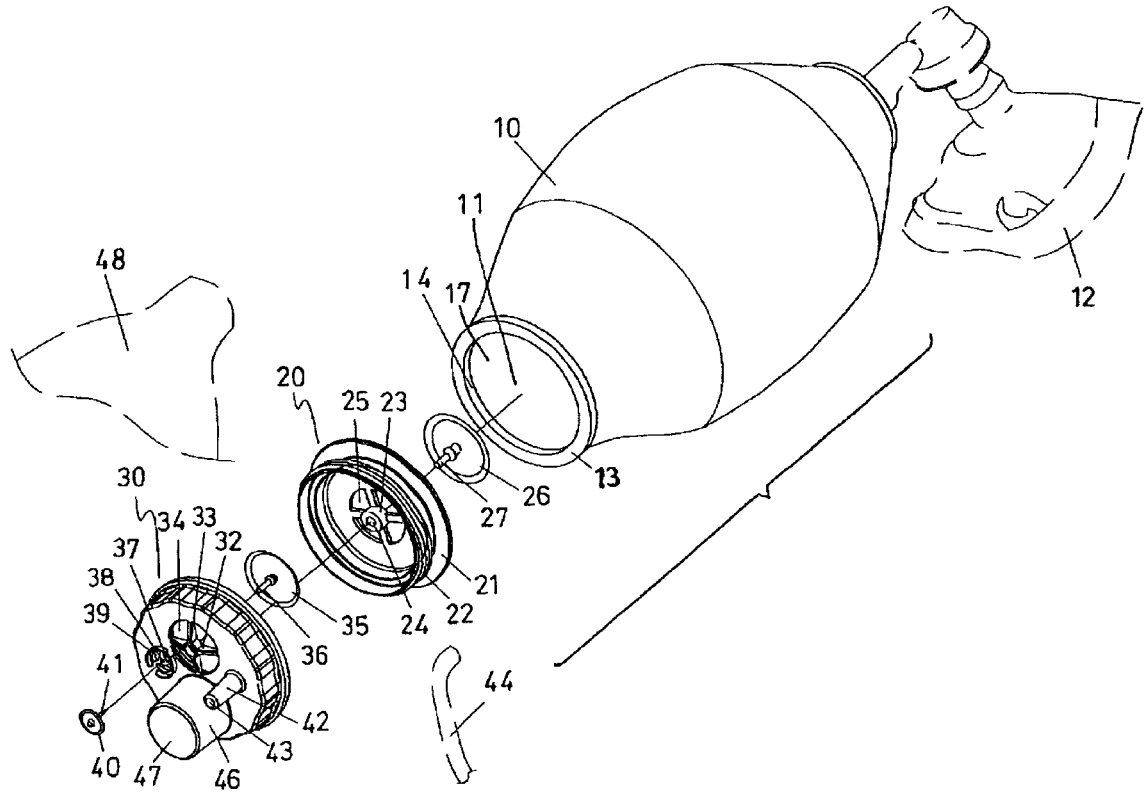

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-4 are cancelled.

* * * * *